United States Patent [19]

Birkle

[11] Patent Number: 5,126,872
[45] Date of Patent: Jun. 30, 1992

[54] APPARATUS FOR OPTICALLY SCANNING THE SURFACE OF AN OBJECT WHOSE SURFACE IS CAPABLE OF REFLECTING OR SCATTERING LIGHT

[75] Inventor: Gebhard Birkle, Constance, Fed. Rep. of Germany

[73] Assignee: Birkle Sensor GmbH & Co., Schwäbisch Gmünd, Fed. Rep. of Germany

[21] Appl. No.: 477,947

[22] PCT Filed: Dec. 9, 1988

[86] PCT No.: PCT/DE88/00758
§ 371 Date: Jul. 23, 1990
§ 102(e) Date: Jul. 23, 1990

[87] PCT Pub. No.: WO89/05468
PCT Pub. Date: Jun. 15, 1989

[51] Int. Cl.⁵ .............................. G02B 26/10
[52] U.S. Cl. .................... 359/196; 359/833; 359/204; 385/119; 355/238; 356/24; 356/385
[58] Field of Search ............ 359/196, 896, 742, 831, 359/204, 850, 851, 858, 868, 833; 385/115, 119; 356/347, 348, 373, 376, 380, 398, 24, 385; 355/240, 234, 238

[56] References Cited

U.S. PATENT DOCUMENTS 3,625,612  12/1971  Decker, Jr. .................... 356/24
4,352,550  10/1982  Uchida ........................... 355/238

FOREIGN PATENT DOCUMENTS 3601442  7/1987  Fed. Rep. of Germany.
55211  3/1985  Japan.
1385912  3/1975  United Kingdom.

OTHER PUBLICATIONS

1981 Carnahan Conference on Crime Countermeasures by G. D. Arndt et al—May 13-15, 1981—pp. 135-141.

Primary Examiner—Loha Ben
Attorney, Agent, or Firm—Peter K. Kontler

[57] ABSTRACT

An apparatus for optically scanning a reflective object includes a first reflector having a frustoconical reflecting surface with a central opening. A second reflector has a flat reflecting surface which faces the frustoconical surface and is inclined with respect to the axis thereof. To the side of the flat surface is an optoelectronic sensor which is connected to a processing unit. Between the sensor and the flat surface is a focusing system which functions to focus light reflected from such surface onto the sensor. In operation, an object to be scanned is moved through the central opening of the frustoconical surface along the axis of the latter. As the object moves, a light source illuminates successive, circumferentially complete bands of the object at a predetermined location within the space surrounded by the frustoconical surface. Light from the source impinges upon the object from laterally thereof and at an angle to the axis of the frustoconical surface. At least a portion of the impinging light is reflected by the object to the frustoconical surface which, in turn, reflects the light to the flat surface. The flat surface directs the light to the focusing system which forms an image of a respective band on the sensor. The image is analyzed by the processing unit to detect irregularities on the surface of the object.

10 Claims, 3 Drawing Sheets

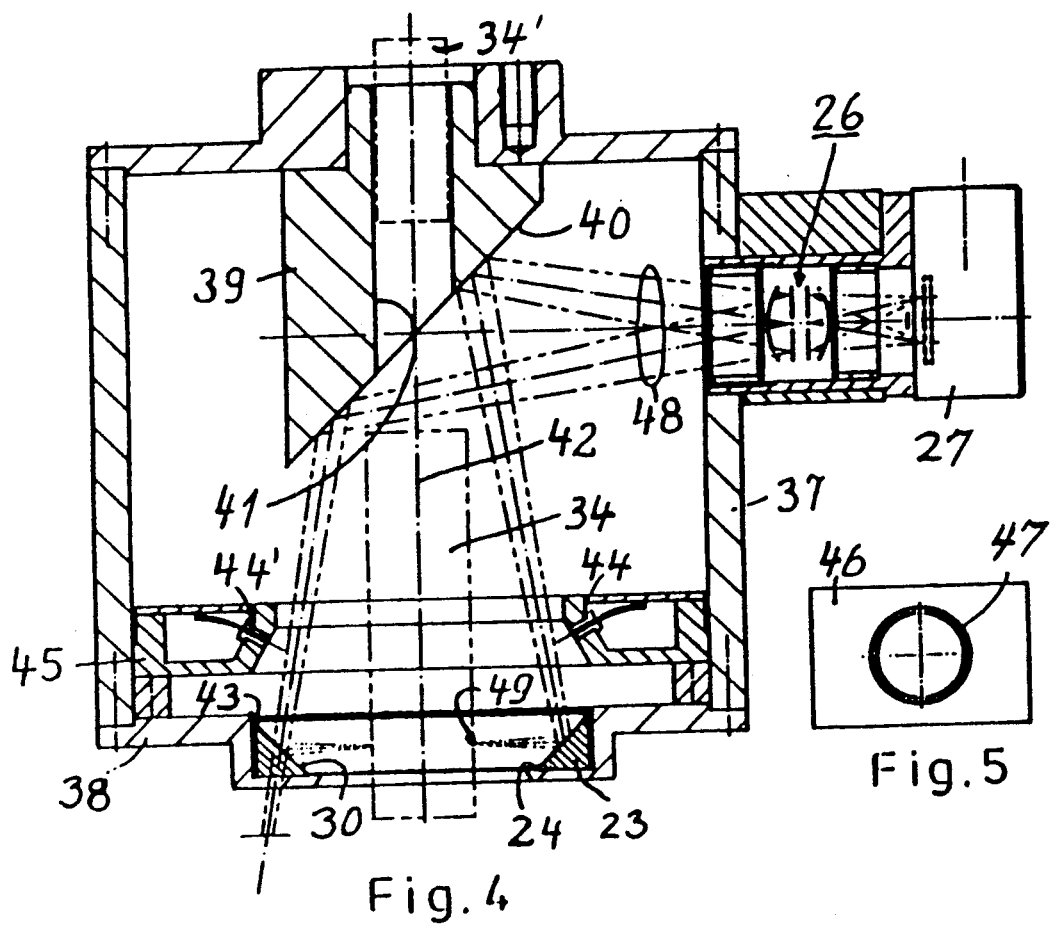
Fig. 4
Fig. 5
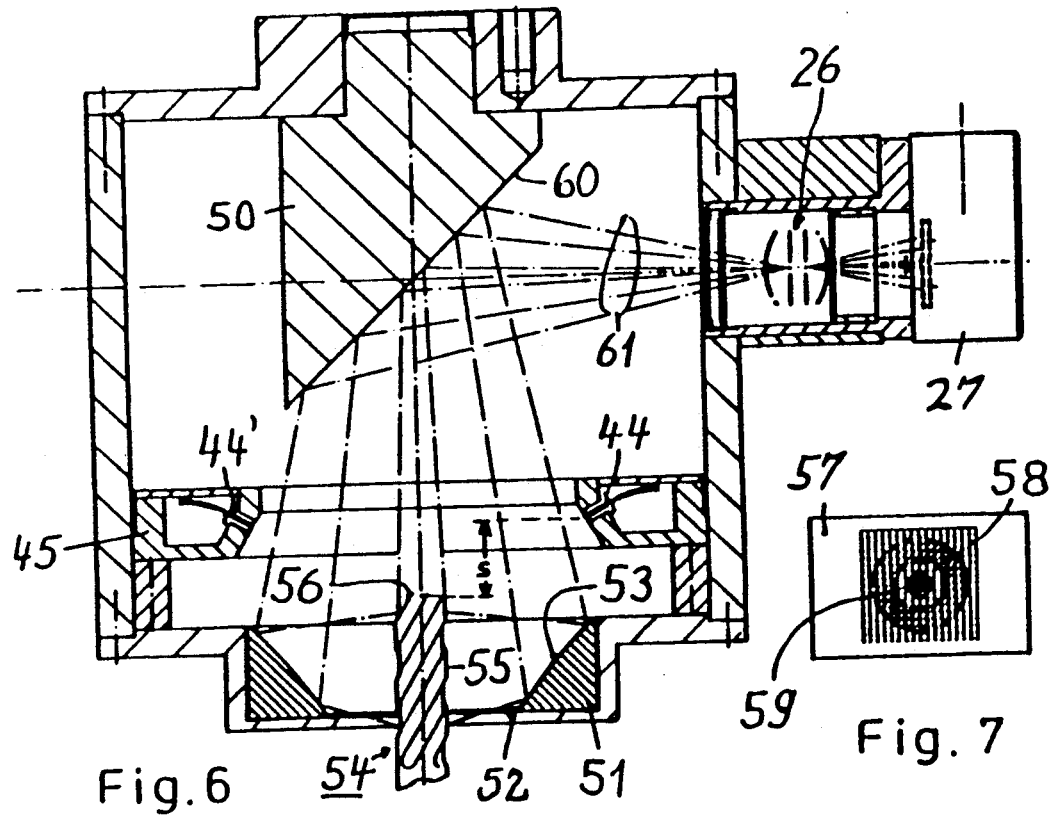
Fig. 6
Fig. 7

APPARATUS FOR OPTICALLY SCANNING THE SURFACE OF AN OBJECT WHOSE SURFACE IS CAPABLE OF REFLECTING OR SCATTERING LIGHT

TECHNICAL FIELD

The invention relates to an apparatus for optically scanning the surface of an object, particularly a transparent, translucent or opaque movable object, having a surface capable of reflecting or scattering light.

PRIOR ART

A scanning device for optically scanning an object point-by-point is known from the West German Publication No. 3601442 and consists of a light source whose light is projected onto the object to be scanned via a deflecting device. Following reflection or transmission through the object, the light is analyzed in a photoelectric analyzing unit. The deflecting device is constituted by a rotating optical system whose axis of rotation coincides with the axis of the incoming light beam and which causes the deflected light beam to rotate in a circular path about the axis of rotation. The scanning beam is parallel to the axis of rotation or makes an angle therewith. The deflecting optical system is a prism rotating at high rpm and having an inclined reflecting surface which projects the scanning beam onto a stationary hollow reflector. The prism is located inside the chamber enclosed by the hollow reflector and on the main axis of the hollow reflector, which coincides with the axis of rotation of the prism, while the object is situated within the opening angle of the hollow reflector. Interiorly of the opening angle of the hollow reflector is a second hollow reflector. The axes of the hollow reflectors coincide and the object is disposed within the opening angle of the second hollow reflector or directly in the chamber enclosed by the second hollow reflector. Since the deflecting optical system undergoes a lifting motion, it is possible to scan the peripheral surface of an object upon rotation. This mode of spatial scanning of the surface of an object is difficult, particularly for small objects. Thus, a large expenditure is required for the optical system and the rotating parts in order to obtain a sharp image thereby resulting in expensive apparatus. It is difficult to generate stationary images of high resolution with deflecting optical systems which move.

The Japanese Publication No. 60-55211 teaches a scanning device of very similar structure for point-by-point scanning of an object. This scanning device likewise has two annular, hollow reflectors which are centered with respect to one another and are arranged one above the other, and a rotating prism with an inclined reflecting surface which projects a rotating light beam onto the upper hollow reflector. The light beam is diverted by the upper hollow reflector and projected onto the second hollow reflector located therebelow. The latter deflects the light beam onto the object. From there, the light travels back again along the same path to a photosensitive sensor.

The U.S. Pat. No. 4,352,550 discloses an arrangement in which a rotating prism having an inclined reflecting surface is located within a ring of optical fibers whose ends face the prism in such a manner that a beam of light reflected from the reflecting surface of the prism is projected onto the ends of the optical fibers. The far ends of the optical fibers are assembled into a linear unit so that a rotating light beam is converted into a light beam which moves back-and-forth. This apparatus exhibits the same drawbacks as the first apparatus described and a moving object can be scanned with neither.

TECHNICAL PROBLEM

It is an object of the invention to provide an apparatus of the technical nature indicated which make it possible to scan the surfaces of objects whose surfaces are capable of reflecting or scattering light, preferably during movement of the objects. An image signal of high resolution is to be obtained so that, as the object moves, a peripheral region of the object having a specific width is reproduced as a peripheral band.

DESCRIPTION OF THE INVENTION

The invention has the outstanding advantage that translucent, transparent or opaque objects of virtually any shape, and whose surfaces are capable of reflecting or scattering light, may be scanned in such a manner that a circumferentially complete or incomplete peripheral region of predetermined width can be converted, during movement of the object, into an image signal of highest resolution representing, for example, a peripheral band or a portion of a peripheral band. The surface of the object can reflect normally or diffusely and the object can have high or low reflectivity. If the surface of the object has irregularities, holes, discontinuities, gouges, chips, damage to edges or other abnormalities, reflection or scattering is changed relative to the normal surface; this change in reflection or scattering can be detected according to the invention.

In particular, the apparatus in accordance with the invention is suitable for examining the surface condition of elongated objects such as screws, nails, pencils, glasses, textile fibers and many others, preferably during movement of the same, in order to sort the objects, for instance, using specified quality criteria. The apparatus can be designed, for example, to detect the surfaces of the objects during free fall or, for a fiber, during continuous through travel. This assures high efficiency of the apparatus of the invention with a large throughput of objects or running meters of object. Of particular advantage is the fact that a peripheral ring of an object and the end face of the object can be optically examined simultaneously.

BRIEF DESCRIPTION OF THE DRAWING

FIG. 4 shows a commercial design for the apparatus of FIG. 1 in which the upper reflecting body is an inclined, flat reflector having a through opening and the optical structural element is a prismatic backscattering reflector having an internal, frustoconical, circumferentially extending reflecting surface with a through opening, the apparatus further including an illuminating device for the object consisting of optical fibers arranged in a circle above the backscattering reflector, and the apparatus also including an optical system and a sensor located behind the same, FIG. 5 shows a schematic illustration of the image of a narrow peripheral ring or a scanning line produced on the sensor of FIG. 4, FIG. 6 shows a commercial design in which the upper reflecting body is an integral, inclined, flat reflector and the optical structural element is a backscattering reflector having an internal, frustoconical, circumferentially extending, convex reflecting surface with a through opening, the apparatus further including an illuminating device as in FIG. 6, an optical system and a sensor behind the latter for forming an image of a peripheral ring as well as the end face of an object, FIG. 7 shows an illustration of the images of the peripheral ring and end face of the object to be scanned as produced per FIG. 6.

MODES OF EXECUTION OF THE INVENTION

Figure 1:
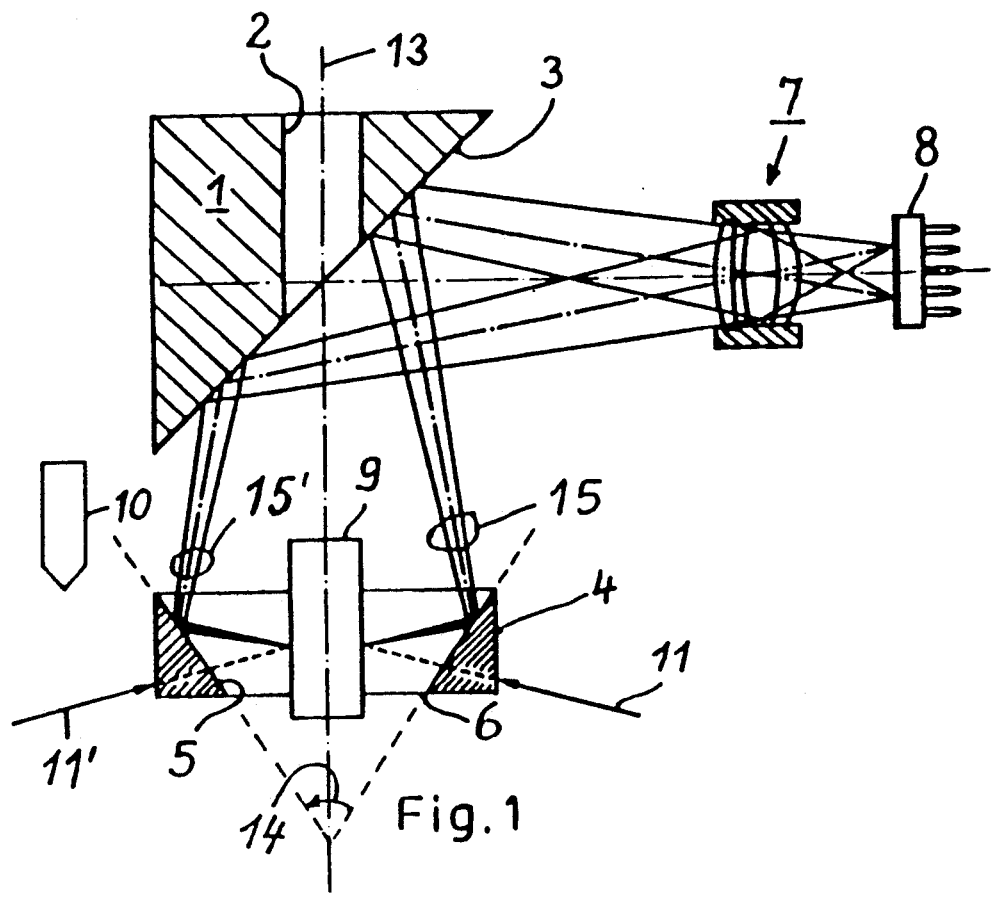
FIG. 1 shows a schematic illustration of an apparatus consisting of two reflecting bodies with through openings, one of the reflecting bodies being constructed as a beam-splitting, backscattering reflector having an internal, frustoconical, circumferentially extending reflecting surface and the other reflecting body being located above the backscattering reflector and having an inclined reflecting surface, the apparatus further including an optical system and a sensor located behind the same, and the object being peripherally illuminated from the side through the backscattering reflector or above the latter.

FIG. 1 schematically shows the design of an apparatus consisting of a lower, prismatic reflecting body 4 having an upper reflecting body 1 disposed above the same with the two being held in vertical alignment. The reflecting bodies 1 and 4 consist of suitable glass having appropriately reflectorized surfaces as reflecting surfaces; the reflecting bodies can likewise be composed of metal having reflectorized metallic surfaces. The reflecting body 1, which is preferably cylindrical with a through opening 2 extending parallel to the main or cylinder axis 13 of the cylinder 1, has an inclined, flat reflecting surface 3 of elliptical contour formed by a plane which cuts the cylinder 1 at an angle.

The reflecting body 4 is constructed as a backscattering reflector whose reflecting surface 5 is preferably an internal, frustoconical, beam-splitting surface and whose main axis coincides with the main axis 13. A through opening 6 extends centrally through the reflecting surface 5 and the reflecting body 4 in the direction of the main axis 13 so that the main axes of the two through openings 2,6 are coincident. The object 9, which may be transparent or translucent or opaque, can be moved through the through openings 2,6, e.g., in free fall, as indicated by the motion arrow 10. An objective 7 for optical imaging is located laterally of the reflecting surface 3 of the reflecting body 1; behind the objective 7 is a sensor 8 which can be in the form of a diode ring or a flat diode, for example, but is preferably constituted by an annular or flat CCD-matrix structural element.

The reflecting body 1 has a diameter which is approximately equal to the largest diameter of the reflecting surface 5 so that the reflecting surfaces 3,5 have about the same size when projected one onto the other. The reflecting body 1 is located within the opening angle 14 of the reflecting surface 5.

The object 9 is illuminated by a plurality of light beams 11,11' surrounding the object 9 in the form of a ring. With reference to the main axis 13 of the passages 2 and 6 of the reflecting bodies 1 and 4, the angle of impingement of the light beams 11,11' on the surface of the object 9 can be different from 90 degrees so that the light beams 11,11' and the main axis 13 of the passages 2,6 for the object 9 are not perpendicular to one another but, instead, the light beams penetrate the main axis 13 at an inclination. The reflecting body 4 can be made transparent in an appropriate manner in the region of impingement of the light beams 11,11'. The light beams 11,11' which surround the object 9 in the form of a ring then pass through the reflecting body 4 and the beam-splitting reflecting surface 5 and fall on the entire circumferentially extending surface of the object 9 within a band of specified width to thereby scan a more or less narrow surface ring. Alternatively, illumination of the object 9 may take place annularly and laterally above the backscattering reflector 4. From there, the light is reflected onto the reflecting surface 5 where scattered light may also arrive. The reflected light 15,15' then travels upwards to fall on the reflecting surface 3 which projects the light onto the objective 7. The latter collects the light and forms an image on the sensor 8 therewith in accordance with the imaging scale. The CCD-matrix structural element, which can be made to operate as a ring or as a plane by means of software, produces an image of the scanned peripheral band of the object 9 in the form of a circular line or area.

If, during the outlined scanning procedure, the object 9 is now moved along the main axis 13 of the apparatus in the direction of the motion arrow 10, it is evident that the entire peripheral surface of the object 9 is scanned and reproduced on the sensor 8, which forms an image of the illuminated peripheral surface, as a circular area which changes with time. Should an irregularity on the surface of the object 9 be illuminated at time t during passage of the object 9 through the reflecting surface 5, this irregularity is synchronously indicated in the circular area of the sensor 8 which represents the peripheral band of the object 9 so that such object can be sorted out, for example.

Figure 2:
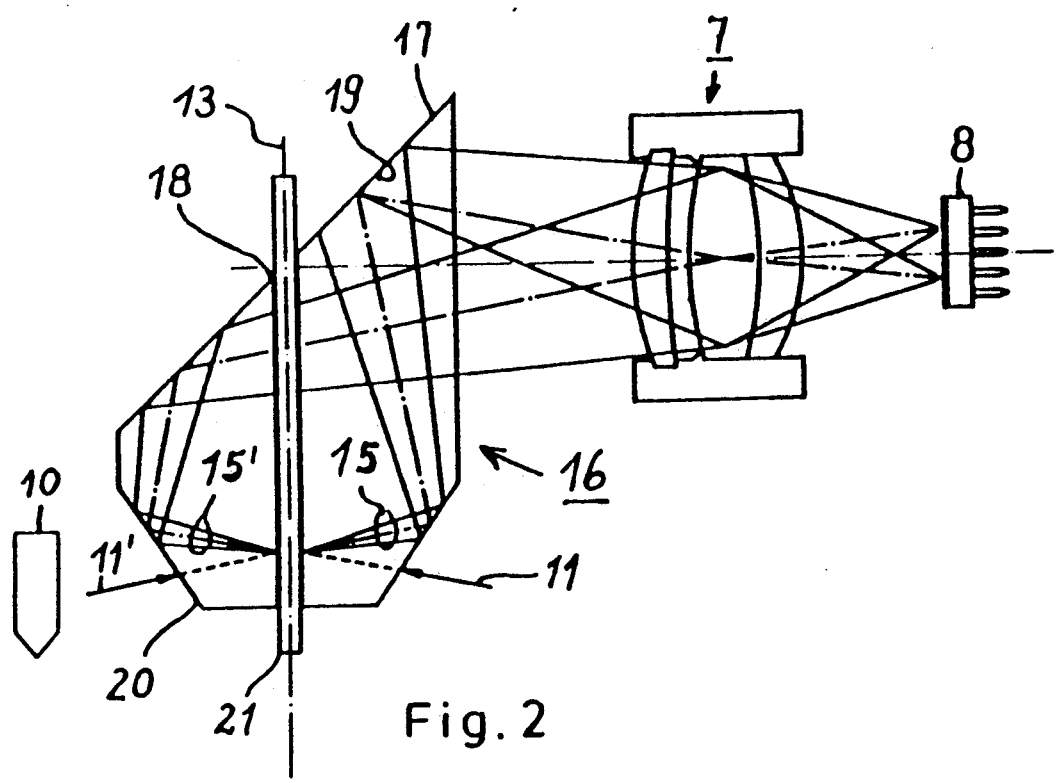
FIG. 2 shows another apparatus with a single reflecting body having an internal, beam-splitting, frustoconical, circumferentially extending reflecting surface, as well as an internal, inclined reflecting surface, for the scanning of elongated objects of relatively small diameter such as, for example, pencils or fibers, which are longer than the reflecting body.

FIG. 2 shows an apparatus which is particularly well-suited for the scanning of long objects such as pencils, or running objects such as fibers, having transparent, translucent or opaque surfaces which must, however, be reflective.

A prismatic reflecting body 16 which is cylindrical, for instance, is provided with an inclined flat 17 having a through opening 18 along the direction of the main axis 13 of the reflecting body 16. The lower end of the reflecting body 16 has a frustoconical bevel which defines a circumferentially extending conical surface. The conical surface is internally reflectorized so as to form a beam-splitting, conical reflecting surface 20. The upper, inclined flat 17 is designed as an internally reflectorized reflecting surface 19 to the side of which is an objective 7 having a sensor 8 in accordance with FIG. 1 behind it; illumination of the object 21 can be carried out in the same manner as described with reference to FIG. 1.

It may be seen from FIG. 2 that the object 21 to be scanned can have a length greater than the height of the reflecting body 16. When the ratio of the diameter of the object 21 to the diameter of the objective 7 does not exceed a specified value, the elongated object 21 acts optically like a slit. Thus, in spite of the fact that the objective 7 is covered to a certain extent by the thickness of the object 21, it is possible to see quasi around the object with a certain loss in brightness. If this ratio between the thickness of the object 21 to be scanned and the diameter of the objective 7 is maintained or not exceeded, there then exists the condition which makes it possible to also scan moving objects such as, for example, fibers, longer than the entire reflecting body.

Figure 3:
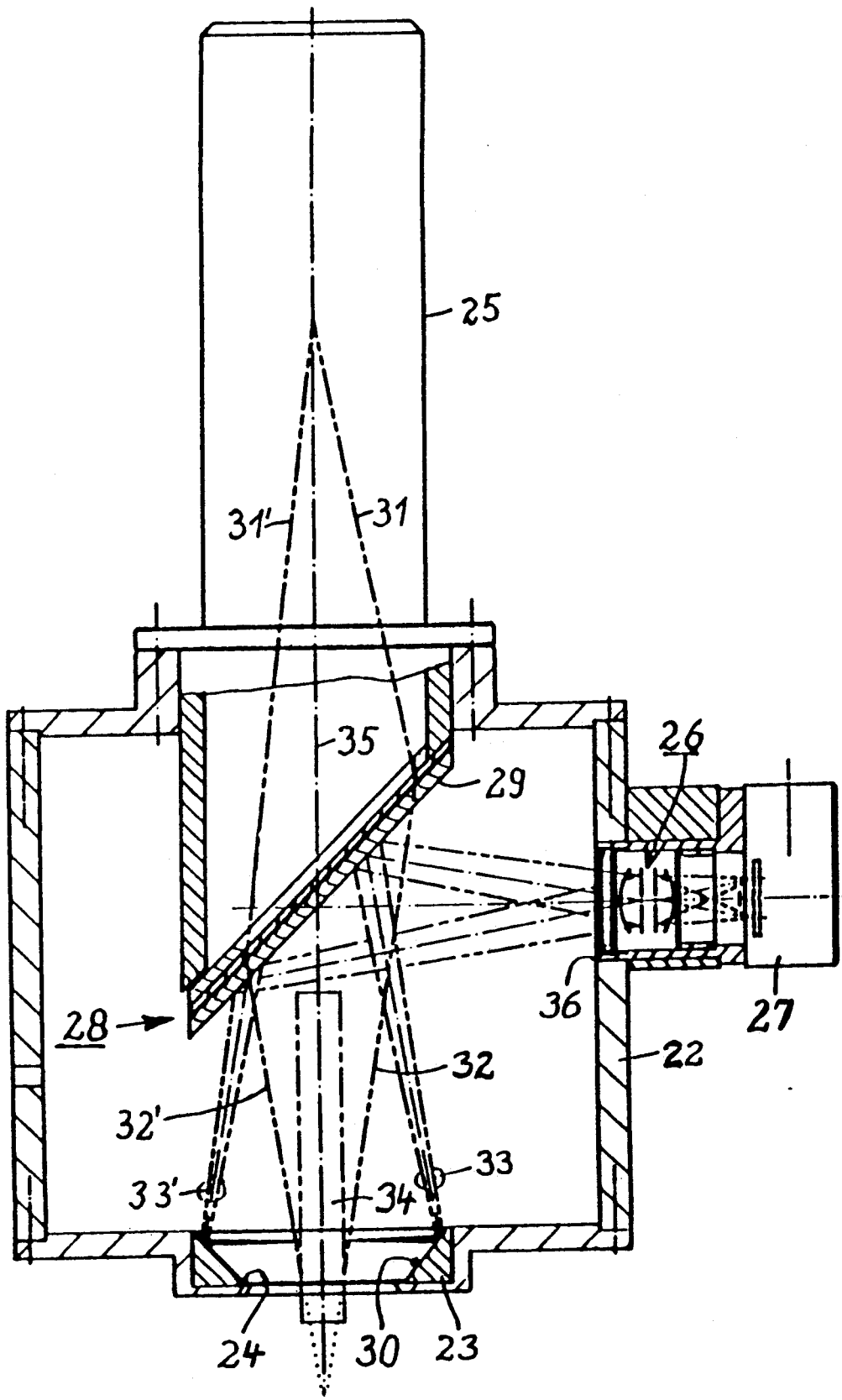
FIG. 3 shows an apparatus similar to that of FIG. 1, the upper reflecting surface here being enclosed and constructed as a holographic lens with a beam-splitting reflector below the same, and the illuminating device being situated directly above the reflector, the light being cast onto the object approximately parallel thereto.

FIG. 3 illustrates an exemplary apparatus consisting of a housing 22 having a backscattering reflector 23 centrally mounted in the lower region thereof. The backscattering reflector 23 can correspond to the reflecting body 4 of FIG. 1 and is provided with a central through opening 24. An illuminating device 25 containing a laser, for example, is located above the housing 22. An optical system 26 is situated to the side of the housing 22 behind a window 36 and a sensor 27 is disposed behind the optical system 26. The sensor 27 is designed like the sensor 8 of FIG. 1 and has an output which is connected to a non-illustrated analyzing unit. A holographic lens 28 is located inside the housing 22 above the backscattering reflector 23 and a beam-splitting reflector 29 is disposed at the underside of the holographic lens 28.

A light packet 31,31' from an illuminating unit 25 passes through the holographic lens 28 and is focused by the same so that the boundary rays 32,32' subsequently impinge upon an object 34 to be scanned at an acute angle as considered with reference to the central axis 35. The object 34 can be moved through the through opening 24 in the backscattering reflector 23. The light beams 33,33' reflected from the surface of the object 34 fall onto the reflecting surface 30 of the backscattering reflector 23, are reflected from there to fall onto the beam-splitting reflector 29 and are then reflected from the latter through the optical system 26 to the sensor 27.

The holographic lens 28 and the beam-splitting reflector 29 do not have a through opening and the object 34 is instead moved below the lens 28 in the through opening 24 of the backscattering reflector 23. However, it is conceivable to design the holographic lens 28 and the beam-splitting reflector 29 with a common through opening. Another possible construction is one in which the holographic lens is replaced by a beam-splitting Fresnel reflector.

In the preceding Figures, the lengths of the boundary light rays of the enclosed light packets are all equal.

FIG. 4 illustrates a commercial design for an apparatus like that of FIG. 1. This consists of a cylindrical housing 37 having a lower housing cover 38 with a central cutout. A backscattering reflector 23 (according to FIG. 3) having an internal, frustoconical, circumferentially extending reflecting surface 30 and a through opening 24 is mounted in the central cutout. The upper reflecting body 39 is provided with an inclined, flat reflecting surface 40 in accordance with FIG. 1 and is disposed opposite an optical system 26 and a sensor 27 situated behind the same. The reflecting body 39 has a through opening 41 for through passage of the object 34' and the main axis 42 is simultaneously the central vertical axis of the backscattering reflector 23 and the reflecting body 39. An object 34 can also be moved through the through opening 24 of the backscattering reflector 23 from below.

Illumination of the objects 34,34' takes place peripherally by means of optical fibers 44,44' located laterally of and above the backscattering reflector 23 and arranged in a ring about the path of the objects 34,34'. The ends of the optical fibers 44,44' can be held by a holder 45 so as to be adjustable in height. The normals to the exit surfaces of the optical fibers 44,44' are preferably not perpendicular to the central axis 42 so that the incoming light falls onto the surface of the object 34 at an angle different from 90 degrees. Further operation of the apparatus is the same as that described with reference to FIGS. 1 and 3.

FIG. 5 shows a CCD-matrix structural element 46 within the sensor 27. The optical system 26 forms a small circular ring 47 on the CCD-matrix structural element 46 from the light 48 reflected by the object 34 and the ring 47 reproduces the peripheral ring 49 scanned on the object 34.

FIG. 6 illustrates a commercial design of an apparatus like that of FIG. 4. Here, an upper, integral reflecting body 50 without a through opening is mounted in the housing and, similarly to the reflecting body 39, has an inclined, flat reflecting surface 60. As in FIG. 4, a backscattering reflector 51 with a through opening 52 is arranged below the reflecting body 50. In contrast to the design of FIG. 4, the inclined, circumferentially extending, internal, frustoconical reflecting surface 53 is here curved along a surface line so that, in cross section, the intersection lines of the reflecting surface 53 are curves rather than straight lines as in the preceding Figures. The reflecting surface 53 has a convex curvature such that the light 61 reflected from the object diverges.

The optical fibers 44,44' located peripherally of and above the backscattering reflector 51 in the form of a ring have a spacing s from the end face 56 of an object 54, e.g., a borer. For scanning, this object 54 is pushed through the central through opening 52 of the backscattering reflector 51 and, by means of the peripheral optical fibers 44,44' arranged in the form of a ring, is illuminated from the side along a peripheral ring 55 while the end face 56 is illuminated from above. In this manner, a relatively wide peripheral ring 55 of the object 54 is scanned simultaneously with the end face 56 of the object 54.

FIG. 7 shows the outcome of the scan as seen on a CCD-matrix structural element 57 within the sensor 27. On the one hand, a relatively wide circular ring 58 corresponding to the peripheral ring 55 of the object 54 is formed. On the other hand, a circular area 59 which reproduces the end face 56 of the object 54 is simultaneously formed centrally of and within the circular ring 58.

The CCD-matrix structural element 57 can be electronically masked by means of software so that the illustrated images of the circular ring 58 and the circular area 59 are retained.

The surface of the backscattering reflector can additionally have a concave curvature so that, in a cross section through such a backscattering reflector, the intersections of the reflecting surface are lines with a concave curvature. Likewise, the backscattering reflector and the reflecting body can together constitute an anamorphic optical system which makes anamorphic imaging possible.

The backscattering reflector described can also consist of a plurality of lenses which surround the object peripherally in the form of a circle and conduct the reflected light to the sensor. If necessary, optical fibers can be arranged between the lenses and the sensor.

INDUSTRIAL UTILITY

On the one hand, the apparatus and method of the invention are especially well-suited for use where a large number of objects, particularly mass produced objects, is to be examined or sorted within a short period of time in accordance with predetermined quality criteria. On the other hand, the apparatus and method of the invention are well-suited for use where the surface condition, including the color, of a running object such as, for example, a textile fiber, is to be determined.

| List of Reference Numerals | |
|---|---|
| 1 | Body |
| 2 | Through Opening |
| 3 | Inclined Reflecting Surface |
| 4 | Conical Prism |
| 5 | Conical Reflecting Surface |
| 6 | Through Opening |
| 7 | Objective |
| 8 | Sensor (CCD-Matrix Structural Element) |
| 9 | Object |
| 10 | Motion Arrow for the Direction of Movement of the Object |
| 11,11' | Incoming Light Beams |
| 13 | Main Axis |
| 14 | Opening Angle |
| 15 | Reflected Light Beams |
| 16 | Prismatic Reflecting Body |
| 17 | Inclined Flat |
| 18 | Through Bore |
| 19 | Inclined, Flat, Internal Reflecting Surface |
| 20 | Conical, Beam-Splitting Reflecting Surface |
| 21 | Object |
| 22 | Housing |
| 23 | Backscattering Reflector |
| 24 | Through Opening |
| 25 | Illuminating Device (Laser) |
| 26 | Optical System |
| 27 | Sensor |
| 28 | Holographic Lens |
| 29 | Reflector with Reflecting Surface |
| 30 | Reflecting Surface |
| 31,31',32,32' | Boundary Rays |
| 33,33' | Reflected Light Beams |
| 34 | Object |
| 35 | Central Axis |
| 36 | Window |
| 37 | Housing |
| 38 | Lower Housing Cover |
| 39 | Reflecting Body |
| 40 | Reflecting Surface |
| 41 | Through Opening |
| 42 | Main Axis |
| 43 | Cutout |
| 44,44' | Optical Fibers |
| 45 | Holder |
| 46 | CCD-Matrix Structural Element |
| 47 | Circular Ring |
| 48 | Reflected Light Beams |
| 49 | Illuminated, Narrow Peripheral Ring on the Object |
| 50 | Reflecting Body |
| 51 | Backscattering Reflector |
| 52 | Through Opening |
| 53 | Reflecting Surface |
| 54 | Object |
| 55 | Peripheral Ring |
| 56 | End Face |
| 57 | CCD-Matrix Structural Element |
| 58 | Circular Ring |
| 59 | Circular Area |
| 60 | Reflecting Surface |
| 61 | Reflected Light Beams |

I claim:

1. Apparatus for optically scanning a surface of a movable object whose surface is capable of reflecting or scattering light, the apparatus having a light source and a conical or bowl-shaped optical, internally reflectorized backscattering reflector which is provided with a circumferentially extending reflecting surface and a through opening centered relative to said surface for passage of the object through the backscattering reflector, a second reflector being located within an opening angle of the backscattering reflector and above said through opening as considered in the direction of a main axis of the backscattering reflector and having a reflecting surface, and the apparatus also having an optoelectronic sensor and an electrical analyzing unit, the light being projected onto the reflecting surfaces of the reflectors following reflection or scattering at the object, deflected to the sensor and analyzed in the analyzing unit, wherein the light source illuminates the object around its entire periphery in the region of the through opening such that the light reflected or scattered from the object around its periphery simultaneously falls on the reflecting surface of the backscattering reflector peripherally, the reflecting surface of said second reflector being an inclined, flat reflecting surface which conducts the reflected or scattered light to an optical system for optical stationary imaging on the sensor, the latter detecting a complete peripheral band corresponding to a peripheral ring of the object.

2. Apparatus according to claim 1, wherein the second reflector above the backscattering reflector has a through opening for the object which is situated directly above the through opening of the backscattering reflector, the axes of the two through openings coinciding.

3. Apparatus according to claim 2, wherein the backscattering reflector is constituted by a prism and the second reflector is constituted by a reflecting body separated from the prism.

4. Apparatus according to claim 2, wherein the two reflectors are formed by a prismatic cylindrical reflecting body and are disposed opposite one another, said prismatic, cylindrical reflecting body having a frusto-conical lower end constituting an internal conical reflector and said prismatic, cylindrical reflecting body having an upper end constituting an inclined, flat reflector with an elliptical reflecting surface.

5. Apparatus according to claim 1, wherein said light source includes optical fibers which peripherally illuminate the object, said optical fibers having ends which are circularly held in a holder which is centrally arranged above the backscattering reflector and surrounds a path of the object through the backscattering reflector in the form of a ring.

6. Apparatus according to claim 1, wherein the reflector above the backscattering reflector is a holographic lens between which and the backscattering reflector is a beam-splitting reflector, the light source being located directly above the holographic lens.

7. Apparatus according to claim 1, wherein the sensor is a CCD-matrix structural element.

8. Apparatus according to claim 1, wherein the backscattering reflector is constituted by a plurality of lenses which are arranged in a circle, surround the object peripherally and conduct the reflected light to the sensor.

9. Apparatus according to claim 8, wherein said light source comprises optical fibers between said lenses and said sensor.

10. Apparatus according to claim 1, wherein the reflector above the backscattering reflector is a beam-splitting Fresnel reflector between which and the backscattering reflector is a beam-splitting reflector, the light source being located directly above the Fresnel reflector.

* * * * *

UNITED STATES PATENT AND TRADEMARK OFFICE
CERTIFICATE OF CORRECTION

PATENT NO. : 5,126,872

DATED : June 30, 1992

INVENTOR(S) : Gebhard Birkle

It is certified that error appears in the above-identified patent and that said Letters Patent is hereby corrected as shown below:

On the title page, Foreign Application Priority Data, should read
--Dec. 10, 1987, Fed. Rep. of Germany, 3741770;
  July 1, 1988, Fed. Rep. of Germany, 3822303.--
Col. 5, line 26, "an" should read --the-- and "unit" should read --device--.

Signed and Sealed this

Thirtieth Day of November, 1993

Attest:

BRUCE LEHMAN

Attesting Officer

Commissioner of Patents and Trademarks